(12) United States Patent
Pattie

(10) Patent No.: US 7,401,984 B2
(45) Date of Patent: Jul. 22, 2008

(54) OPTICAL CONNECTOR

(75) Inventor: Robert Alan Pattie, Nyora (AU)

(73) Assignees: Hoya Corporation, Tokyo (JP);
Optiscan Pty Ltd., Notting Hill (AU)

( * ) Notice: Subject to any disclaimer, the term of this patent is extended or adjusted under 35 U.S.C. 154(b) by 678 days.

(21) Appl. No.: 10/845,223

(22) Filed: May 14, 2004

(65) Prior Publication Data

US 2005/0025499 A1    Feb. 3, 2005

Related U.S. Application Data

(60) Provisional application No. 60/470,874, filed on May 16, 2003.

(51) Int. Cl.
*G02B 6/36* (2006.01)
*G02B 6/38* (2006.01)

(52) U.S. Cl. .............. 385/89; 385/55; 385/70; 385/71; 385/88

(58) Field of Classification Search .......... 385/15, 385/24, 53, 55, 70, 71, 88–94
See application file for complete search history.

(56) References Cited

U.S. PATENT DOCUMENTS

| | | | |
|---|---|---|---|
| 5,120,953 A | 6/1992 | Harris | 250/227.2 |
| 5,161,053 A | 11/1992 | Dabbs | 359/384 |
| 5,323,009 A | 6/1994 | Harris | 250/458.1 |
| 5,742,419 A | 4/1998 | Dickensheets et al. | 359/201 |
| 5,907,425 A | 5/1999 | Dickensheets et al. | 359/224 |
| 6,456,381 B1 * | 9/2002 | Nakamura et al. | 356/483 |
| 6,490,395 B1 * | 12/2002 | Nara et al. | 385/39 |
| 6,616,343 B2 * | 9/2003 | Katsura et al. | 385/55 |
| 6,741,776 B2 * | 5/2004 | Iwashita et al. | 385/49 |
| 6,760,521 B2 * | 7/2004 | Watanabe | 385/50 |
| 6,860,648 B2 * | 3/2005 | Jin et al. | 385/89 |
| 7,040,814 B2 * | 5/2006 | Morimoto et al. | 385/88 |
| 2001/0031116 A1 * | 10/2001 | Katsura et al. | 385/55 |
| 2003/0026554 A1 * | 2/2003 | Jin et al. | 385/89 |

* cited by examiner

*Primary Examiner*—Sung Pak
*Assistant Examiner*—Daniel Petkovsek
(74) *Attorney, Agent, or Firm*—Greenblum & Bernstein, P.L.C.

(57) ABSTRACT

An optical connector for use with a light separator, the optical connector including a first portion and a second portion, the first portion being optically couplable by first optical transmitter to a first input of the light separator and by second optical transmitter to a second input of the light separator. The first and second portions are detachably couplable to couple the first and second optical transmitter to third and fourth optical transmitters, respectively, provided in or coupled to the second portion. The first and second inputs of the light separator can thereby be optically coupled to a first optical instrument coupled to the third optical transmitter and a second optical instrument coupled to the fourth optical transmitter.

20 Claims, 3 Drawing Sheets

OPTICAL CONNECTOR

RELATED APPLICATIONS

This application is based on and claims the benefit of the filing date of U.S. provisional application Ser. No. 60/470,874 filed 16 May 2003, the contents of which is incorporated herein by reference in its entirety.

FIELD OF THE INVENTION

The present invention relates to an optical connector, of particular but by no means exclusive application with endoscopes, endomicroscopes, microscopes, colonoscopes and scanning devices for connecting an optical coupler to both a laser and a detector unit.

BACKGROUND OF THE INVENTION

An arrangement typical of existing endoscopes is shown schematically at 10 in FIG. 1. The laser 12 provides the excitation light for a fluorescent dye with which a sample has been stained or for reflection from the sample. A light separator in the form of coupler 14 couples laser light from the laser 12 to both endoscope head 16 and a power monitor 18. The power monitor 18 includes a power monitor device, and allows the operator to obtain some measure of the power being delivered to the endoscope head 16. The coupler 14 also couples the light returned by the sample (from low level excited fluorescence and/or reflection) back to a detection unit 20, which contains a barrier filter and a photomultiplier tube (not shown) to detect this return light. The core of optical fiber 22 between the endoscope head 16 and the coupler 14 is the transmission medium for both the excitation light and the return signal but, in some prior art systems, also constitutes a spatial filter (or, in effect, a pinhole) so that confocal detection may be effected.

In such arrangements, the laser 12, coupler 14, power monitor 18 and detection unit 20 are provided in a control box 24. Optical fiber 22 is detachably coupled to the control box 24 by means of an optical connector (not shown), so that the endoscope head 16 can be detached, such as for cleaning, between successive patients, or the like, by detaching the single optical connection between the control box 24 and that portion of the endoscope (i.e. optical fiber 22 and endoscope head 16) outside the control box.

Such arrangements have a number of problems. The relative power between the endoscope head 16 and the photodiode of the power monitor 18 is dependent on any joint loss at the connection between control box 24 to optical fiber 22 (due, for example, to dust in the connection). This means that the power monitor 18 needs, in principle, to be calibrated each time a new or replacement endoscope head 16 is connected. Where a 488 nm laser is used, it is necessary to ensure low loss at this interface for both the 488 nm excitation light and the 488 to 585 nm return light, as light of all these wavelengths is carried by optical fiber 22; the connection is between single mode fiber and requires low loss in both directions.

Further, this connection can affect the mode mix and hence the optical power distribution in optical fiber 22, which has the potential to produce image instability, noise and reduced resolution. In addition, reflection from this connection can cause instability in laser 12 resulting in image noise, and increase noise in the ultimate image by reflecting excitation light into the detection unit 20.

SUMMARY OF THE INVENTION

In a first broad aspect, the present invention provides an optical connector for use with a light separator, the optical connector comprising:
 a first portion and a second portion, said first portion being optically couplable by first optical transmitter to a first input of said light separator and by second optical transmitter to a second input of said light separator;
 wherein said first and second portions are detachably couplable to couple said first and second optical transmitters to respectively third and fourth optical transmitters provided in or coupled to said second portion, whereby said first and second inputs of said light separator can be optically coupled to a first optical instrument coupled to said third optical transmitter and a second optical instrument coupled to said fourth optical transmitter.

It will be understood, however, that—while the connector may generally be used with at least two optical instruments—in some applications only one optical instrument may be so coupled. Also, it will be understood that an optical instrument can comprise any device that is adapted to provide optical output or receive optical input.

In one embodiment, said optical instruments respectively comprise a laser source and a light detector, wherein said laser source is optically couplable by the third optical transmitter to said second portion and said light detector is optically couplable by the fourth optical transmitter to said second portion, whereby said first optical transmitter can be coupled via said third optical transmitter to said laser source and said second optical transmitter can be coupled via said fourth optical transmitter to said light detector.

The light separator is typically in the form of an optical coupler.

In this embodiment, at least a portion of each of said first and second optical transmitter is preferably integral with, or permanently connected during manufacture to, said light separator (or coupler).

Each optical transmitter preferably comprises an optical fiber (though possibly incorporating a join). More preferably, each of said optical fibers is single or few mode with the exception of said fourth optical transmitter which can be multimode, few mode or single mode for coupling to a light detector.

When multimode the fourth optical transmitter has a greater diameter and many more guided modes than the second optical transmitter, so that alignment of the second and fourth optical fibers is more readily effected while achieving low loss.

In certain embodiments, the optical connector is adapted to couple more than two pairs of optical transmitters, each of said first and said second portions being optically couplable by one or more further optical transmitters to one or more respective further inputs of said light separator.

The invention also provides in a further aspect an optical apparatus comprising:
 a light separator;
 a power monitor;
 a first portion of an optical connector that comprises said first portion and a second portion, said first portion being optically couplable by first optical transmitter to a first input of said light separator and by second optical transmitter to a second input of said light separator, said first portion being detachably couplable to said second portion to couple said first and second optical transmitters to respectively third and fourth optical transmitters provided in or coupled to said second portion;

wherein said light separator is optically coupled or couplable to an optical head, said power monitor and said first portion, whereby said apparatus is detachably couplable to said second portion.

In one particular embodiment, the optical apparatus further comprises a housing enclosing said light separator and said power monitor, and either supporting said first portion or at least partially enclosing said first portion.

Thus, the second portion will typically be coupled in use to a laser source and a light detector, but such an arrangement can be used to facilitate cleaning or sterilisation; this apparatus can be decoupled from the laser source and light detector and another comparable apparatus substituted while the first is cleaned.

The optical apparatus may further comprise the optical head.

The light separator may be permanently coupled to said power monitor. This permits more reliable calibration of the system, as the efficiency of light transmission between the light separator and the power monitor should remain constant.

In another aspect, the invention provides an optical scanning system including an optical connector as described above.

In a still further aspect, the invention provides an endoscope including an optical connector as described above.

In a still further aspect, the invention provides an endomicroscope including an optical connector as described above.

In yet another aspect, the invention provides a microscope including an optical connector as described above.

The invention also provides a method for providing an optical connection comprising employing an optical connector as described above.

BRIEF DESCRIPTION OF THE DRAWINGS

In order that the invention may be more clearly ascertained, an embodiment will now be described, by way of example, with reference to the accompanying drawings, in which.

DETAILED DESCRIPTION

Figure 1:
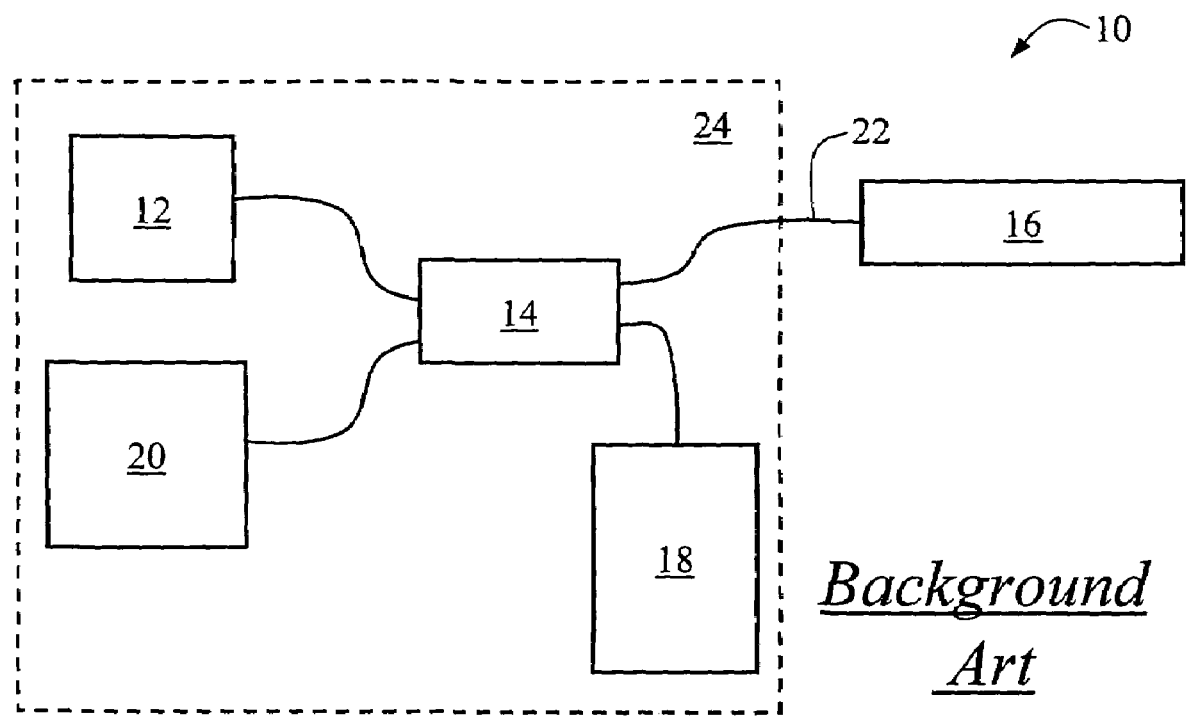
FIG. 1 is a schematic view of a background art endoscope.
Figure 2:
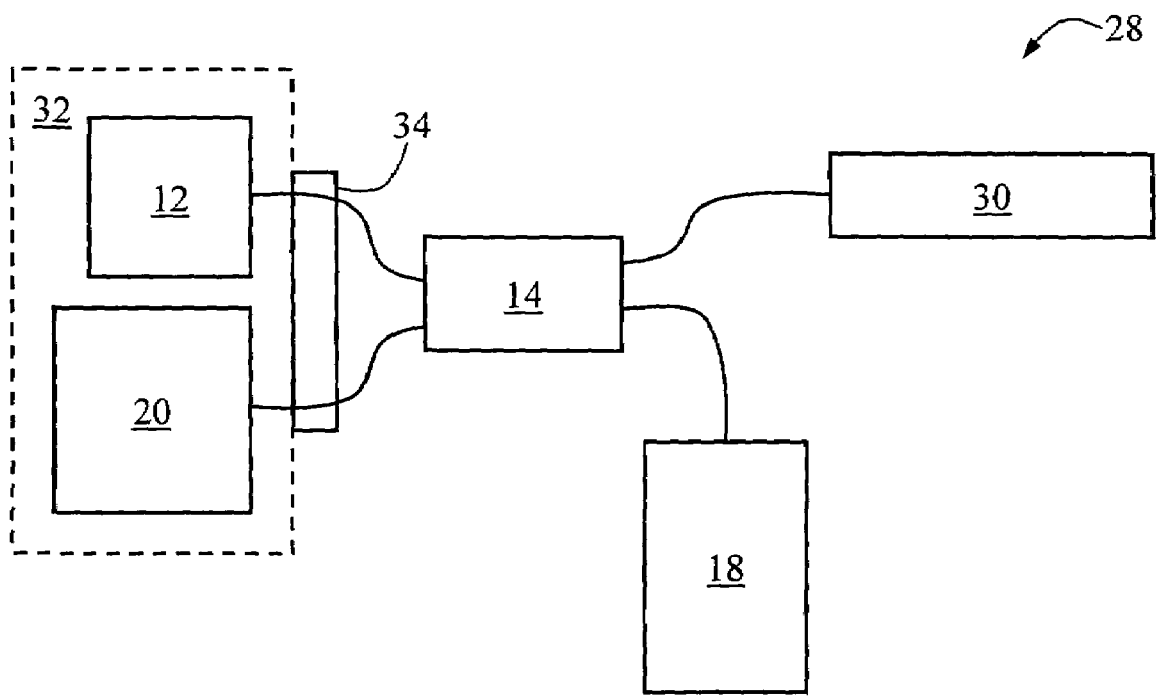
FIG. 2 is a schematic view of an endoscope incorporating an optical connector according to an embodiment of the present invention.

An optical scanning system incorporating an optical connector according to an embodiment of the present invention is shown generally at 28 in FIG. 2. The components of scanning system 28 are, in some cases, comparable with those of endoscope 10 of FIG. 1, so like reference numerals have been used to indicates like features.

Scanning system 28, which might be in the form of an endoscope or microscope, includes a laser 12 with 488 nm wavelength output, a light separator in the form of coupler 14, a scanning optical head 30, power monitor 18, and detection unit 20. Laser 12 and detection unit 20 are contained in control box 32.

Figure 3:
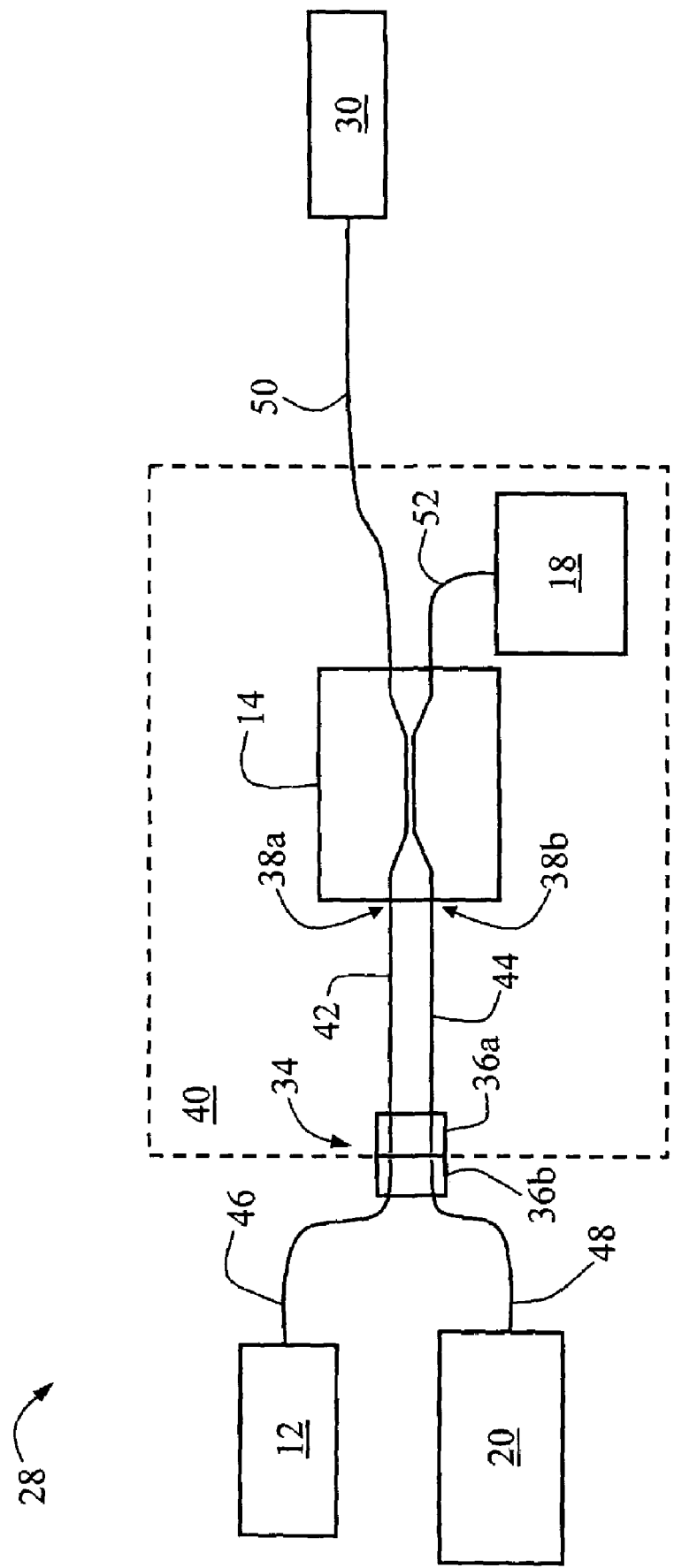
FIG. 3 is another schematic view of the endoscope of FIG. 2.

Scanning system 28 is also provided with an optical connector 34 for connecting the coupler 14 to the control box 32. Referring to FIG. 3, which is a more detailed schematic view of scanning system 28 of FIG. 2, the connector 34 comprises two portions, first portion 36a and second portion 36b. The first portion 36a is coupled to first and second inputs 38a, 38b of the coupler 14 by means of optical transmitters in the form of, respectively, first optical fiber 42 and second optical fiber 44, while the second portion 36b forms a part of the control box 32 and is coupled to the laser 12 and the detection unit 20 by means of optical transmitters in the form of, respectively, third optical fiber 46 and fourth optical fiber 48. It will be understood that first and second inputs 38a, 38b of coupler 14 are points that may equivalently be referred to as "outputs" since light can—in principle even if not in this embodiment—pass in both directions past these points, and because first optical fiber 42 and second optical fiber 44 are integral with the coupler 14 at these points. Further, it will be understood that second portion 36b need not be a part of or directly connected to the control box 32.

The coupler 14 is coupled to the scanning optical head 30 by means of an optical transmitter in the form of fifth optical fiber 50, and to power monitor 18 by means of an optical transmitter in the form of sixth optical fiber 52. In this embodiment, fifth optical fiber 50 and sixth optical fiber 52 are integral with coupler 14.

All the optical fibers (with the exception of fourth optical fiber 48) are single mode (in fact of SM450 fiber) at the wavelength of laser 12.

Consequently, the connection from third optical fiber 46 to first optical fiber 42 provides a stable split ratio of the light from the laser 12, to provide class compliance, stable illumination of the sample at the scanning system 28, and a power distribution of light illuminating the sample that minimizes degradation of optical resolution.

Similarly, this means that only one fiber is used in the coupler 14, which provides strong optical power exchange from one fiber to the other in the coupler waist region, though—in some applications—dissimilar fibers forming an asymmetric coupler could be used acceptable or indeed advantageous.

Fourth optical fiber 48 could also be single or few mode, but as it is merely necessary that there be low loss for light travelling to the detection unit 20, a larger core multimode fiber is used so that the alignment tolerance is relaxed. Care should be exercised, however, to avoid excessive mode dispersion in fourth optical fiber 48 or imaging sensitivity may be reduced.

Thus, in this embodiment fourth optical fiber 48 is a multimode fiber having a considerably greater core diameter than have the other optical fibers, by at least an order of magnitude. In particular, it has a substantially larger core diameter than the second optical fiber 44 to which—in use—it is optically coupled. Consequently, when the connector 34 is connected (that is, portions 36a and 36b are coupled), the fourth optical fiber 48 and the second optical fiber 44 will be readily aligned as long as the more difficult alignment—between single mode first optical fiber 42 and single mode third optical fiber 46—has been effected. This reduces the engineering challenge associated with constructing such a connector if only single mode fibers (with core diameters of perhaps 5 μm or less) were employed; this would require, during the physical coupling of the two portions 36a and 36b of the connector 34, precise alignment of exceedingly small cores.

Figure 4:
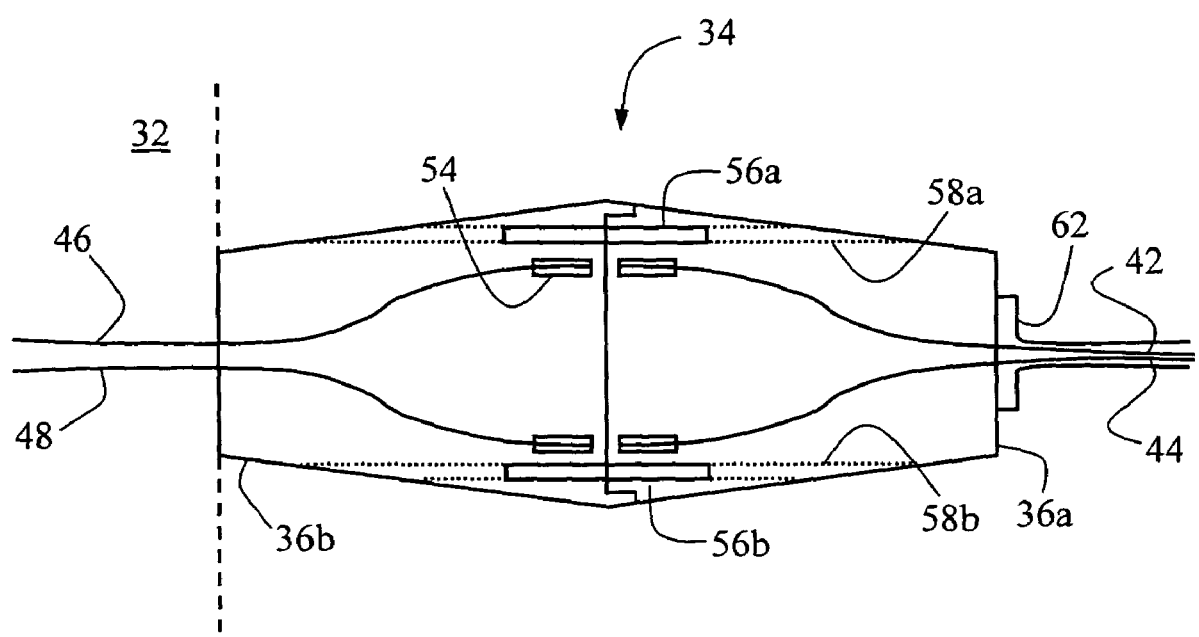
FIG. 4 is a schematic view of the connector of the endoscope of FIG. 2.

The connector 34 is shown schematically in greater detail in FIG. 4. Within each of the two portions 36a and 36b of connector 34, the tips of first, second, third, and fourth fibers 42, 44, 46 and 48 are located within metal ferrules (such as ferrule 54 of third optical fiber 46), so that each tip can be positioned accurately for alignment with the opposite tip. The two portions 36a and 36b of connector 34 are aligned by means of a pair of positioning pins 56a, 56b accessible for coupling and decoupling via a pair of slots 58a, 58b in the sides of the connector 34.

The two portions 36a and 36b of connector 34 are held together by any suitable means; this could be in the form of pins, grub screws, or an external clip attached to one portion for engaging the other portion.

First and second optical fibers 42 and 44 transmit light to and from coupler 14 (see FIG. 3), so are enclosed in a common protective sheath 62.

Thus, in use the connector 34 allows the quick detachment of the scanning optical head 30, power monitor 18 and coupler 14 as a single unit. This means that replacement units must include more components than the endoscope head 16 of the background art arrangement of FIG. 1, but with the following advantages that—in some applications—are expected to make this approach desirable.

Indeed, first portion 36a of connector 34, coupler 14 and power monitor 18 and associated fibers 42, 44, 52 can all be contained in a physical housing 40 (from which fifth optical fiber 50 and hence optical head 30 would protrude) that an operator can easily attach and detach from second portion 36b of connector 34. The housing 40 can consequently be sealed for ready sterilisation and cleaning. In such an embodiment, the scanning system 28 might be in the form of an endoscope or colonoscope, where sterilisation and cleaning are particularly important considerations. The physical housing 40 and its contents thus constitute an optical apparatus for use as a part of, for example, an endoscope, endomicroscopes or colonoscope.

Input excitation light transmitted to power monitor 18 and scanning optical head 30 passes through only one connection that, in use, is decoupled and recoupled (i.e. the connection from third optical fiber 46 to first optical fiber 42). Consequently, the power delivered to both the power monitor 18 and the scanning optical head 30 will have a constant relationship that is independent of loss in connector 34: this relationship will not be affected by a change in the total power delivered to first optical fiber 42 (such as due to dust coming between the tips of third optical fiber 46 to first optical fiber 42). As a result, it is not necessary to provide an additional set-up test when connecting a (possibly) sterilised scanning optical head 30 before use to ensure class compliance or accurate power setting.

Wavelength performance of the optical joint formed by the connector 34 is easier to achieve. This is because the connection between third optical fiber 46 and first optical fiber 42 is from single mode fiber to single mode fiber and only needs low loss at the 488 nm wavelength of laser 12 in the forward direction, while the connection between second optical fiber 44 and fourth optical fiber 48 is only required to have low loss for 488 to 585 nm wavelength light transmitted in the return direction only. In the background art arrangement of FIG. 1, low loss would be required for both 488 nm excitation light and 488 to 585 nm return light, so the connection in optical fiber 22 at the outside of control box 24 is necessarily (in this example) between two segments of single mode fiber requiring low loss in both directions.

Further, optical loss at the connection between second and fourth optical fibers 44, 48 for low level fluorescence may, in some applications, be lower in the present embodiment than at a connection in optical fiber 22 at the outside of control box 24 in the background art arrangement of FIG. 1.

Modifications within the scope of the invention may be readily effected by those skilled in the art. For example, the embodiment illustrated in FIGS. 2 to 4 comprises a scanning system, but the same approach can clearly be employed in an endoscope, a microscope and an endomicroscope. It is to be understood, therefore, that this invention is not limited to the particular embodiments described by way of example hereinabove.

Further, any reference herein to prior art is not intended to imply that such prior art forms or formed a part of the common general knowledge.

I claim:

1. An optical connector for use with a light separator, said optical connector comprising:

a first portion and a second portion, said first portion being optically couplable by first optical transmitter to a first input of said light separator and by second optical transmitter to a second input of said light separator;

wherein said first and second portions are detachably couplable to couple said first and second optical transmitters to respectively third and fourth optical transmitters provided in or coupled to said second portion, and wherein said first, second, third and fourth optical transmitters comprise first, second, third and fourth optical fibers respectively, said fourth optical fiber being multimode and having a greater diameter and many more guided modes than said second optical fiber;

whereby said first and second inputs of said light separator can be optically coupled to a first optical instrument coupled to said third optical transmitter and a second optical instrument coupled to said fourth optical transmitter, and alignment of said second and said fourth optical fibers can be readily effected while achieving low loss.

2. An optical connector as claimed in claim 1, wherein said optical instruments respectively comprise a laser source and a light detector, wherein said laser source is optically couplable by the third optical transmitter to said second portion and said light detector is optically couplable by the fourth optical transmitter to said second portion, whereby said first optical transmitter can be coupled via said third optical transmitter to said laser source and said second optical transmitter can be coupled via said fourth optical transmitter to said light detector.

3. An optical connector as claimed in claim 1, wherein said light separator is in the form of an optical coupler.

4. An optical connector as claimed in claim 1, wherein at least a portion of said first optical transmitter and at least a portion of said second optical transmitter are integral with, or permanently connected during manufacture to, said light separator.

5. An optical connector as claimed in claim 4, further comprising the light separator.

6. An optical connector as claimed in claim 4, further comprising a power monitor optically coupled to said light separator.

7. An optical connector as claimed in claim 6, wherein said power monitor is permanently coupled to said light separator.

8. An optical connector as claimed in claim 1, wherein said optical connector is adapted to couple more than two pairs of optical transmitters, each of said first and said second portions being optically couplable by one or more further optical transmitters to one or more respective further inputs of said light separator.

9. An optical scanning system including an optical connector according to claim 1.

10. An endoscope including an optical connector according to claim 1.

11. An endomicroscope including an optical connector according to claim 1.

12. A microscope including an optical connector according to claim 1.

13. An optical apparatus comprising:
   a light separator;
   a power monitor; and
   a first portion of an optical connector that comprises said first portion and a second portion, said first portion being optically couplable by first optical transmitter to a first input of said light separator and by second optical transmitter to a second input of said light separator, said first portion being detachably couplable to said second portion to couple said first and second optical transmitters to respectively third and fourth optical transmitters provided in or coupled to said second portion;
   wherein said light separator is optically coupled or couplable to an optical head, said power monitor and said first portion, whereby said apparatus is detachably couplable to said second portion.

14. An optical apparatus as claimed in claim 13, further comprising a housing enclosing said light separator and said power monitor, and either supporting said first portion or at least partially enclosing said first portion.

15. An optical apparatus as claimed in claim 13, further comprising said optical head.

16. An optical apparatus as claimed in claim 13, wherein said light separator is permanently coupled to said power monitor.

17. An endoscope comprising an optical apparatus according to claim 13.

18. An endomicroscope comprising an optical apparatus according to claim 13.

19. A microscope comprising an optical apparatus according to claim 13.

20. A method for providing an optical connection comprising:
   providing an optical connector comprising a first portion and a second portion, said first portion being optically couplable by a first optical transmitter to a first input of a light separator and by a second optical transmitter to a second input of said light separator; and
   coupling said first and second portions in order to couple said first and second optical transmitters to respectively third and fourth optical transmitters provided in or coupled to said second portion;
   wherein said first, second, third and fourth optical transmitters comprise first, second, third and fourth optical fibers respectively, said fourth optical fiber being multimode and having a greater diameter and many more guided modes than said second optical fiber;
   whereby said first and second inputs of said light separator can be optically coupled to a first optical instrument coupled to said third optical transmitter and a second optical instrument coupled to said fourth optical transmitter, and alignment of said second and said fourth optical fibers can be readily effected while achieving low loss.

* * * * *